(12) United States Patent
Forssmann et al.

(10) Patent No.: US 6,180,773 B1
(45) Date of Patent: Jan. 30, 2001

(54) TANDEM CDNAS ENCODING CHEMOKINES CC-1, CC-2, AND CC-3

(75) Inventors: Wolf-Georg Forssmann, Feodor-Lynen-Str. 31, Hannover (DE), 30625; Andreas Pardigol, Hannover (DE); Hans-Jürgen Mägert, Hannover (DE); Peter Schulz-Knappe, Hannover (DE)

(73) Assignee: Wolf-Georg Forssmann, Hannover (DE)

(*) Notice: Under 35 U.S.C. 154(b), the term of this patent shall be extended for 0 days.

(21) Appl. No.: 09/180,077

(22) PCT Filed: Apr. 30, 1997

(86) PCT No.: PCT/EP97/02217

§ 371 Date: Dec. 30, 1998

§ 102(e) Date: Dec. 30, 1998

(87) PCT Pub. No.: WO97/41230

PCT Pub. Date: Nov. 6, 1997

(30) Foreign Application Priority Data

Apr. 30, 1994 (DE) ............................... 196 17 312

(51) Int. Cl.⁷ .................. C12N 15/19; C07K 14/52; A61K 38/19
(52) U.S. Cl. .................. 536/23.51; 530/350; 530/351; 514/2; 424/85.1
(58) Field of Search .................. 536/23.51; 530/350, 530/351; 514/2; 424/85.1

(56) References Cited

U.S. PATENT DOCUMENTS 5,874,211 * 2/1999 Bandman et al. ................ 435/6

FOREIGN PATENT DOCUMENTS

| | | |
|---|---|---|
| 19512463A1 | 10/1996 | (DE) . |
| 95/17092 * | 6/1995 | (WO) . |
| 95/18228 | 7/1995 | (WO) . |
| 96/16979 | 6/1996 | (WO) . |
| 96/34891 | 11/1996 | (WO) . |
| 97/21812 * | 6/1997 | (WO) . |

OTHER PUBLICATIONS

Pardigol, A., et al. (1998) *Proc. Nat'l Acad. Sci. USA* 95: 6308–13, May 1998.*
Schulz–Knappe, P., et al. (1996) *J. Exp. Med.* 183: 295–99, Jan. 1996.*
Schulz–Knappe et al., "HCC–1, a Novel Chemokine from Human Plasma", *Journal of Experimental Medicine*, 183(1):295–299 (1996).

* cited by examiner

*Primary Examiner*—David L. Fitzgerald
(74) *Attorney, Agent, or Firm*—Jacobson, Price, Holman & Stern, PLLC

(57) ABSTRACT

The CC type chemokines belong to a family of polypeptides which have proven to be mediators of immune reactions, and they have recently attracted attention due to their antiviral activity with respect to HIV. The cloning and molecular characterization of a human tandem gene is disclosed which contains the closely linked coding regions for two new CC type chemokines the sequences of which are highly homologous with that of MIP-1α. The transcription of the tandem gene leads to a bicistronic mature transcript which contains the non-overlapping open reading frames for the recently described factor HCC-1 and an as yet unknown CC type chemokine, designated as CC-2. Moreover, alternative splicing of the primary transcript yields at least one additional CC type chemokine, cytokine CC-3. Two functional promoter regions were identified within the tandem gene. The disclosed data provide some basic knowledge about the structure and expression of the new human CC-2/HCC-1 tandem gene and describe a mechanism according to which the coexpression of closely linked genes could be regulated in higher eucaryotes.

15 Claims, No Drawings

SEQUENCE LISTING

<160> NUMBER OF SEQ ID NOS: 12

<210> SEQ ID NO 1
<211> LENGTH: 925
<212> TYPE: DNA
<213> ORGANISM: Homo sapiens

<400> SEQUENCE: 1

-continued

| | |
|---|---|
| ccaggaagca gtgagcccag gagtcctcgg ccagccctgc ctgcccacca ggaggatgaa | 60 |
| ggtctccgtg gctgccctct cctgcctcat gcttgttgct gtccttggat cccaggccca | 120 |
| gttcacaaat gatgcagaga cagagttaat gatgtcaaag cttccactgg aaaatccagt | 180 |
| agttctgaac agctttcact ttgctgctga ctgctgcacc tcctacatct cacaaagcat | 240 |
| cccgtgttca ctcatgaaaa gttattttga acgagcagc gagtgctcca agccaggtgt | 300 |
| catattcctc accaagaagg ggcggcaagt ctgtgccaaa cccagtggtc cgggagttca | 360 |
| ggattgcatg aaaaagctga agccctactc aatataataa taaagagaca aagaggcca | 420 |
| gccacccacc tccaacacct cctgagcctc tgaagctccc accaggccag ctctcctccc | 480 |
| acaacagctt cccacagcat gaagatctcc gtggctgcca ttcccttctt cctcctcatc | 540 |
| accatcgccc tagggaccaa gactgaatcc tcctcacggg gaccttacca ccctcagag | 600 |
| tgctgcttca cctacactac ctacaagatc ccgcgtcagc ggattatgga ttactatgag | 660 |
| accaacagcc agtgctccaa gcccggaatt gtcttcatca ccaaaagggg ccattccgtc | 720 |
| tgtaccaacc ccagtgacaa gtgggtccag gactatatca aggacatgaa ggagaactga | 780 |
| gtgacccaga aggggtggcg aaggcacagc tcagagacat aaagagaaga tgccaaggcc | 840 |
| ccctcctcca cccaccgcta actctcagcc ccagtcaccc tcttggagct tccctgcttt | 900 |
| gaattaaaga ccactcatgc tcttc | 925 |

<210> SEQ ID NO 2
<211> LENGTH: 973
<212> TYPE: DNA
<213> ORGANISM: Homo sapiens

<400> SEQUENCE: 2

| | |
|---|---|
| ccaggaagca gtgagcccag gagtcctcgg ccagccctgc ctgcccacca ggaggatgaa | 60 |
| ggtctccgtg gctgccctct cctgcctcat gcttgttgct gtccttggat cccaggccca | 120 |
| gttcacaaat gatgcagaga cagagttaat gatgtcaaag cttccactgg aaaatccagt | 180 |
| agttctgaac agctttcact ttgctgctga ctgctgcacc tcctacatct cacaaagcat | 240 |
| cccgtgttca ctcatgaaaa gttattttga acgagcagc gagtgctcca agccaggtgt | 300 |
| catattcctc accaagaagg ggcggcaagt ctgtgccaaa cccagtggtc cgggagttca | 360 |
| ggattgcatg aaaaagctga agccctactc aatataataa taaagagaca aagaggcca | 420 |
| gccacccacc tccaacacct cctgagcctc tgaagctccc accaggccag ctctcctccc | 480 |
| acaacagctt cccacagcat gaagatctcc gtggctgcca ttcccttctt cctcctcatc | 540 |
| accatcgccc tagggaccaa gactgaatcc tcctcacaaa ctgggggaa accgaaggtt | 600 |
| gttaaaatac agctaaagtt ggtgggggga ccttaccacc cctcagagtg ctgcttcacc | 660 |
| tacactacct acaagatccc gcgtcagcgg attatggatt actatgagac caacagccag | 720 |
| tgctccaagc ccggaattgt cttcatcacc aaaaggggcc attccgtctg taccaacccc | 780 |
| agtgacaagt gggtccagga ctatatcaag gacatgaagg agaactgagt gacccagaag | 840 |
| gggtggcgaa ggcacagctc agagacataa agagaagatg ccaaggcccc ctcctccacc | 900 |
| caccgctaac tctcagcccc agtcaccctc ttggagcttc cctgctttga attaaagacc | 960 |
| actcatgctc ttc | 973 |

<210> SEQ ID NO 3
<211> LENGTH: 339
<212> TYPE: DNA
<213> ORGANISM: Homo sapiens -continued

<400> SEQUENCE: 3

| | | |
|---|---|---|
| atgaaggtct ccgtggctgc cctctcctgc ctcatgcttg ttgctgtcct tggatcccag | 60 |
| gcccagttca caaatgatgc agagacagag ttaatgatgt caaagcttcc actggaaaat | 120 |
| ccagtagttc tgaacagctt tcactttgct gctgactgct gcacctccta catctcacaa | 180 |
| agcatcccgt gttcactcat gaaaagttat tttgaaacga gcagcgagtg ctccaagcca | 240 |
| ggtgtcatat tcctcaccaa gaaggggcgg caagtctgtg ccaaacccag tggtccggga | 300 |
| gttcaggatt gcatgaaaaa gctgaagccc tactcaata | 339 |

<210> SEQ ID NO 4
<211> LENGTH: 279
<212> TYPE: DNA
<213> ORGANISM: Homo sapiens

<400> SEQUENCE: 4

| | | |
|---|---|---|
| atgaagatct ccgtggctgc cattcccttc ttcctcctca tcaccatcgc cctagggacc | 60 |
| aagactgaat cctcctcacg ggaccttac caccoctcag agtgctgctt cacctacact | 120 |
| acctacaaga tcccgcgtca gcggattatg gattactatg agaccaacag ccagtgctcc | 180 |
| aagcccggaa ttgtcttcat caccaaaagg ggccattccg tctgtaccaa ccccagtgac | 240 |
| aagtgggtcc aggactatat caaggacatg aaggagaac | 279 |

<210> SEQ ID NO 5
<211> LENGTH: 722
<212> TYPE: DNA
<213> ORGANISM: Homo sapiens
<220> FEATURE:
<221> NAME/KEY: CDS
<222> LOCATION: (1..339, 444..722)

<400> SEQUENCE: 5

| | |
|---|---|
| atg aag gtc tcc gtg gct gcc ctc tcc tgc ctc atg ctt gtt gct gtc<br>Met Lys Val Ser Val Ala Ala Leu Ser Cys Leu Met Leu Val Ala Val<br>1               5                   10                  15 | 48 |
| ctt gga tcc cag gcc cag ttc aca aat gat gca gag aca gag tta atg<br>Leu Gly Ser Gln Ala Gln Phe Thr Asn Asp Ala Glu Thr Glu Leu Met<br>            20                  25                  30 | 96 |
| atg tca aag ctt cca ctg gaa aat cca gta gtt ctg aac agc ttt cac<br>Met Ser Lys Leu Pro Leu Glu Asn Pro Val Val Leu Asn Ser Phe His<br>        35                  40                  45 | 144 |
| ttt gct gct gac tgc tgc acc tcc tac atc tca caa agc atc ccg tgt<br>Phe Ala Ala Asp Cys Cys Thr Ser Tyr Ile Ser Gln Ser Ile Pro Cys<br>    50                  55                  60 | 192 |
| tca ctc atg aaa agt tat ttt gaa acg agc agc gag tgc tcc aag cca<br>Ser Leu Met Lys Ser Tyr Phe Glu Thr Ser Ser Glu Cys Ser Lys Pro<br>65                  70                  75                  80 | 240 |
| ggt gtc ata ttc ctc acc aag aag ggg cgg caa gtc tgt gcc aaa ccc<br>Gly Val Ile Phe Leu Thr Lys Lys Gly Arg Gln Val Cys Ala Lys Pro<br>                85                  90                  95 | 288 |
| agt ggt ccg gga gtt cag gat tgc atg aaa aag ctg aag ccc tac tca<br>Ser Gly Pro Gly Val Gln Asp Cys Met Lys Lys Leu Lys Pro Tyr Ser<br>            100                 105                 110 | 336 |
| ata taataataaa gagacaaaag aggccagcca cccacctcca acacctcctg<br>Ile | 389 |
| agcctctgaa gctcccacca ggccagctct cctcccacaa cagcttccca cagc atg<br>                                                                              Met | 446 |

```
aag atc tcc gtg gct gcc att ccc ttc ttc ctc ctc atc acc atc gcc      494
Lys Ile Ser Val Ala Ala Ile Pro Phe Phe Leu Leu Ile Thr Ile Ala
115                 120                 125                 130 cta ggg acc aag act gaa tcc tcc tca cgg gga cct tac cac ccc tca      542
Leu Gly Thr Lys Thr Glu Ser Ser Ser Arg Gly Pro Tyr His Pro Ser
            135                 140                 145 gag tgc tgc ttc acc tac act acc tac aag atc ccg cgt cag cgg att      590
Glu Cys Cys Phe Thr Tyr Thr Thr Tyr Lys Ile Pro Arg Gln Arg Ile
        150                 155                 160 atg gat tac tat gag acc aac agc cag tgc tcc aag ccc gga att gtc      638
Met Asp Tyr Tyr Glu Thr Asn Ser Gln Cys Ser Lys Pro Gly Ile Val
    165                 170                 175 ttc atc acc aaa agg ggc cat tcc gtc tgt acc aac ccc agt gac aag      686
Phe Ile Thr Lys Arg Gly His Ser Val Cys Thr Asn Pro Ser Asp Lys
180                 185                 190 tgg gtc cag gac tat atc aag gac atg aag gag aac                      722
Trp Val Gln Asp Tyr Ile Lys Asp Met Lys Glu Asn
195                 200                 205
```

<210> SEQ ID NO 6
<211> LENGTH: 113
<212> TYPE: PRT
<213> ORGANISM: Homo sapiens

<400> SEQUENCE: 6

```
Met Lys Val Ser Val Ala Ala Leu Ser Cys Leu Met Leu Val Ala Val
1               5                   10                  15

Leu Gly Ser Gln Ala Gln Phe Thr Asn Asp Ala Glu Thr Glu Leu Met
            20                  25                  30

Met Ser Lys Leu Pro Leu Glu Asn Pro Val Val Leu Asn Ser Phe His
        35                  40                  45

Phe Ala Ala Asp Cys Cys Thr Ser Tyr Ile Ser Gln Ser Ile Pro Cys
    50                  55                  60

Ser Leu Met Lys Ser Tyr Phe Glu Thr Ser Ser Glu Cys Ser Lys Pro
65                  70                  75                  80

Gly Val Ile Phe Leu Thr Lys Lys Gly Arg Gln Val Cys Ala Lys Pro
                85                  90                  95

Ser Gly Pro Gly Val Gln Asp Cys Met Lys Lys Leu Lys Pro Tyr Ser
            100                 105                 110

Ile
```

<210> SEQ ID NO 7
<211> LENGTH: 93
<212> TYPE: PRT
<213> ORGANISM: Homo sapiens

<400> SEQUENCE: 7

```
Met Lys Ile Ser Val Ala Ala Ile Pro Phe Phe Leu Leu Ile Thr Ile
1               5                   10                  15

Ala Leu Gly Thr Lys Thr Glu Ser Ser Ser Arg Gly Pro Tyr His Pro
            20                  25                  30

Ser Glu Cys Cys Phe Thr Tyr Thr Thr Tyr Lys Ile Pro Arg Gln Arg
        35                  40                  45

Ile Met Asp Tyr Tyr Glu Thr Asn Ser Gln Cys Ser Lys Pro Gly Ile
    50                  55                  60

Val Phe Ile Thr Lys Arg Gly His Ser Val Cys Thr Asn Pro Ser Asp
65                  70                  75                  80
```

Lys Trp Val Gln Asp Tyr Ile Lys Asp Met Lys Glu Asn
                85                  90

<210> SEQ ID NO 8
<211> LENGTH: 339
<212> TYPE: DNA
<213> ORGANISM: Homo sapiens

<400> SEQUENCE: 8
atgaaggtct ccgtggctgc cctctcctgc ctcatgcttg ttgctgtcct tggatcccag    60
gcccagttca caaatgatgc agagacagag ttaatgatgt caaagcttcc actggaaaat   120
ccagtagttc tgaacagctt tcactttgct gctgactgct gcacctccta catctcacaa   180
agcatcccgt gttcactcat gaaaagttat tttgaaacga gcagcgagtg ctccaagcca   240
ggtgtcatat tcctcaccaa gaaggggcgg caagtctgtg ccaaacccag tggtccggga   300
gttcaggatt gcatgaaaaa gctgaagccc tactcaata                          339

<210> SEQ ID NO 9
<211> LENGTH: 327
<212> TYPE: DNA
<213> ORGANISM: Homo sapiens

<400> SEQUENCE: 9
atgaagatct ccgtggctgc cattcccttc ttcctcctca tcaccatcgc cctagggacc    60
aagactgaat cctcctcaca aactgggggg aaaccgaagg ttgttaaaat acagctaaag   120
ttggtggggg gaccttacca cccctcagag tgctgcttca cctacactac ctacaagatc   180
ccgcgtcagc ggattatgga ttactatgag accaacagcc agtgctccaa gcccggaatt   240
gtcttcatca ccaaaagggg ccattccgtc tgtaccaacc ccagtgacaa gtgggtccag   300
gactatatca aggacatgaa ggagaac                                       327

<210> SEQ ID NO 10
<211> LENGTH: 770
<212> TYPE: DNA
<213> ORGANISM: Homo sapiens
<220> FEATURE:
<221> NAME/KEY: CDS
<222> LOCATION: (1..339, 444..770)

<400> SEQUENCE: 10 atg aag gtc tcc gtg gct gcc ctc tcc tgc ctc atg ctt gtt gct gtc     48
Met Lys Val Ser Val Ala Ala Leu Ser Cys Leu Met Leu Val Ala Val
 1               5                  10                  15 ctt gga tcc cag gcc cag ttc aca aat gat gca gag aca gag tta atg     96
Leu Gly Ser Gln Ala Gln Phe Thr Asn Asp Ala Glu Thr Glu Leu Met
            20                  25                  30 atg tca aag ctt cca ctg gaa aat cca gta gtt ctg aac agc ttt cac    144
Met Ser Lys Leu Pro Leu Glu Asn Pro Val Val Leu Asn Ser Phe His
        35                  40                  45 ttt gct gct gac tgc tgc acc tcc tac atc tca caa agc atc ccg tgt    192
Phe Ala Ala Asp Cys Cys Thr Ser Tyr Ile Ser Gln Ser Ile Pro Cys
    50                  55                  60 tca ctc atg aaa agt tat ttt gaa acg agc agc gag tgc tcc aag cca    240
Ser Leu Met Lys Ser Tyr Phe Glu Thr Ser Ser Glu Cys Ser Lys Pro
65                  70                  75                  80 ggt gtc ata ttc ctc acc aag aag ggg cgg caa gtc tgt gcc aaa ccc    288
Gly Val Ile Phe Leu Thr Lys Lys Gly Arg Gln Val Cys Ala Lys Pro
                85                  90                  95 agt ggt ccg gga gtt cag gat tgc atg aaa aag ctg aag ccc tac tca    336

```
Ser Gly Pro Gly Val Gln Asp Cys Met Lys Lys Leu Lys Pro Tyr Ser
            100                 105                 110
ata taataataaa gagacaaaag aggccagcca cccacctcca acacctcctg          389
Ile agcctctgaa gctcccacca ggccagctct cctcccacaa cagcttccca cagc atg    446
                                                              Met aag atc tcc gtg gct gcc att ccc ttc ttc ctc ctc atc acc atc gcc    494
Lys Ile Ser Val Ala Ala Ile Pro Phe Phe Leu Leu Ile Thr Ile Ala
115             120                 125                 130 cta ggg acc aag act gaa tcc tcc tca caa act ggg ggg aaa ccg aag    542
Leu Gly Thr Lys Thr Glu Ser Ser Ser Gln Thr Gly Gly Lys Pro Lys
            135                 140                 145 gtt gtt aaa ata cag cta aag ttg gtg ggg gga cct tac cac ccc tca    590
Val Val Lys Ile Gln Leu Lys Leu Val Gly Gly Pro Tyr His Pro Ser
        150                 155                 160 gag tgc tgc ttc acc tac act acc tac aag atc ccg cgt cag cgg att    638
Glu Cys Cys Phe Thr Tyr Thr Thr Tyr Lys Ile Pro Arg Gln Arg Ile
165                 170                 175 atg gat tac tat gag acc aac agc cag tgc tcc aag ccc gga att gtc    686
Met Asp Tyr Tyr Glu Thr Asn Ser Gln Cys Ser Lys Pro Gly Ile Val
180                 185                 190 ttc atc acc aaa agg ggc cat tcc gtc tgt acc aac ccc agt gac aag    734
Phe Ile Thr Lys Arg Gly His Ser Val Cys Thr Asn Pro Ser Asp Lys
195                 200                 205                 210 tgg gtc cag gac tat atc aag gac atg aag gag aac                    770
Trp Val Gln Asp Tyr Ile Lys Asp Met Lys Glu Asn
                215                 220

<210> SEQ ID NO 11
<211> LENGTH: 113
<212> TYPE: PRT
<213> ORGANISM: Homo sapiens

<400> SEQUENCE: 11

Met Lys Val Ser Val Ala Ala Leu Ser Cys Leu Met Leu Val Ala Val
 1               5                  10                  15

Leu Gly Ser Gln Ala Gln Phe Thr Asn Asp Ala Glu Thr Glu Leu Met
             20                  25                  30

Met Ser Lys Leu Pro Leu Glu Asn Pro Val Val Leu Asn Ser Phe His
         35                  40                  45

Phe Ala Ala Asp Cys Cys Thr Ser Tyr Ile Ser Gln Ser Ile Pro Cys
     50                  55                  60

Ser Leu Met Lys Ser Tyr Phe Glu Thr Ser Ser Glu Cys Ser Lys Pro
 65                  70                  75                  80

Gly Val Ile Phe Leu Thr Lys Lys Gly Arg Gln Val Cys Ala Lys Pro
                 85                  90                  95

Ser Gly Pro Gly Val Gln Asp Cys Met Lys Lys Leu Lys Pro Tyr Ser
            100                 105                 110

Ile

<210> SEQ ID NO 12
<211> LENGTH: 109
<212> TYPE: PRT
<213> ORGANISM: Homo sapiens

<400> SEQUENCE: 12

Met Lys Ile Ser Val Ala Ala Ile Pro Phe Phe Leu Leu Ile Thr Ile
```

-continued

| 1 | | | | 5 | | | | | 10 | | | | | 15 | | |
|---|---|---|---|---|---|---|---|---|---|---|---|---|---|---|---|---|
| Ala | Leu | Gly | Thr | Lys | Thr | Glu | Ser | Ser | Ser | Gln | Thr | Gly | Gly | Lys | Pro |
| | | | 20 | | | | | 25 | | | | | 30 | | |
| Lys | Val | Val | Lys | Ile | Gln | Leu | Lys | Leu | Val | Gly | Gly | Pro | Tyr | His | Pro |
| | | 35 | | | | | 40 | | | | | 45 | | | |
| Ser | Glu | Cys | Cys | Phe | Thr | Tyr | Thr | Thr | Tyr | Lys | Ile | Pro | Arg | Gln | Arg |
| | 50 | | | | | 55 | | | | | 60 | | | | |
| Ile | Met | Asp | Tyr | Tyr | Glu | Thr | Asn | Ser | Gln | Cys | Ser | Lys | Pro | Gly | Ile |
| 65 | | | | | 70 | | | | 75 | | | | | | 80 |
| Val | Phe | Ile | Thr | Lys | Arg | Gly | His | Ser | Val | Cys | Thr | Asn | Pro | Ser | Asp |
| | | | | 85 | | | | | 90 | | | | | 95 | |
| Lys | Trp | Val | Gln | Asp | Tyr | Ile | Lys | Asp | Met | Lys | Glu | Asn | | | |
| | | | 100 | | | | | 105 | | | | | | | |

TANDEM CDNAS ENCODING CHEMOKINES CC-1, CC-2, AND CC-3

The present invention relates to the nucleic acid of a tandem gene coding for two polypeptides of the cytokine class, to cytokines CC-2 and CC-3 and their biologically active fragments and/or derivatives, to a medicament containing the peptides according to the invention, to a diagnostic agent, to the use of cytokines CC-2 and CC-3 for medicinal indications, and to a nucleic acid probe which will hybridize to a polynucleotide coding for cytokines CC-2 or CC-3 or a fragment thereof.

The CC type chemokines belong to a family of polypeptides which have proven to be mediators of immune reactions, and they have recently attracted attention due to their antiviral activity with respect to HIV.

The chemokines are small, basic, heparin-binding polypeptides which participate in the induction of immune reactions and in inflammatory processes (1, 2). The first members of this family were cloned from stimulated tonsillary lymphocytes or macrophages in the middle of the eighties. The family is subdivided into CXC and CC chemokines according to the relative positions of the first two cysteine residues. Most of the CXC and CC chemokines exhibit chemotaxis with respect to cells which participate in immune reactions. Some CC chemokines show multiple biological activities, such as control of the proliferation and differentiation of hematopoetic progenitor cells (5, 6, 7, 8, 9), activation and attraction of a wide range of immune cells (10, 11), and postulated participation in HIV-1 and HIV-2 replication control in CD4+ T lymphocytes (12). The most frequently described and best studied CC chemokines in the above described context include MIP-1α, MIP-1β and RANTES. The subdivision of the chemokines into CC and CXC chemokines is also reflected in the structure and position of their genes on the chromosomes (14, 15, 16, 17). Genes of human CXC chemokines are generally found on chromosome 4 and consist of four exons and three introns, whereas the genes of CC chemokines lie on the human chromosome 17 and exhibit a conserved structure with three exons and two introns (18, 19). In 1995, a new type of chemokines has been discovered: the so-called C family which is represented by murine lymphotactin (20). This finding shows that the chemokines are not restricted to only two subfamilies.

The present invention relates, inter alia, to the cloning of a human tandem gene, and to the corresponding mature bicistronic mRNA which contains the open reading frames (ORFs) for a new CC chemokine with six cysteine residues, CC-2, and for the above described factor HCC-1. This factor was isolated from human hemofiltrate, and it has been shown to circulate in high levels in the human plasma of healthy subjects (1–5 nM) and of patients suffering from renal failure (5–80 nM) (21). Unlike other, related CC chemokines, HCC-1 fails to exhibit chemoactivity towards monocytes, and it only stimulates slightly the intracellular $Ca^{2+}$ mobilization, and the release of enzymes in these cells. Further, it was reported that HCC-1 promoted the proliferation of CD34+ bone marrow stem cells in a dose-dependent way (21). Despite of the activities described for HCC-1, its major biological function remains unclear.

The nucleic acid of a human tandem gene according to the invention codes for two new CC type chemokines the sequences of which are somewhat homologous with that of MIP-1α.

Thus the present invention relates to nucleic acids corresponding to the tandem gene having the nucleotide sequences shown in SEQ ID NO: 1, encoding the chemokines designated CC-2 (SEQ ID NO: 6) and CC-1 (SEQ ID NO: 7), and in SEQ ID NO: 2, encoding chemokines CC-2 (SEQ ID NO: 11) and CC-3 (SEQ ID NO: 12).

The transcription of the tandem gene leads to a bicistronic mature transcript which contains the non-overlapping open reading frames for the recently described factor HCC-1 and for CC-2. Moreover, alternative splicing of the primary transcript yields at least one additional CC type chemokine, cytokine CC-3. The present invention also relates to these new CC type cytokines as well as their biologically active amidated, acetylated, phosphorylated and/or glycosylated derivatives.

Two functional promoter regions were identified within the tandem gene. Their ability to induce the expression of the tandem gene was examined. The acquired data provide some basic knowledge about the structure and expression of the new human CC-2/HCC-1 tandem gene and describe a mechanism according to which the coexpression of closely linked genes could be regulated in higher eucaryotes.

The present invention also relates to a medicament containing cytokine CC-2 and/or CC-3 as well as their biologically active amidated, acetylated, phosphorylated and/or glycosylated derivatives as the active ingredient. The medicament is administered in accordance with appropriate galenics, adapted to its way of administration. As usual with peptides, the medicament according to the invention can be administered via parenteral, intravenous, intramuscular, intranasal or bucal routes. The amount of peptide to be administered is between 10 and 3000 μg per unit dose.

The diagnostic agent according to the invention contains polyclonal or monoclonal antibodies against the peptide according to the invention, optionally in a fluorescence-labeled or radiolabeled form, to be employed in per se known assays such as ELISA or RIA.

The diagnostic agent according to the invention may contain nucleic acids coding for the cytokines, mRNA, the nucleic acid according to the invention or fragments thereof, or poly- or oligonucleotides capable of hybridizing to the nucleic acid coding for the cytokines CC-2 and/or CC-3.

The peptides cytokine CC-2 and/or CC-3 according to the invention can be used for the preparation of a medicament for the treatment of disorders of cell migration, diseases of the immune system, tumors and dysfunction of regulatory growth functions.

The present invention also relates to nucleic acid probes which are capable of hybridizing to the nucleic acid according to the invention under stringent conditions.

The full length cDNA of the sequence of the bicistronic CC-2/HCC-1 cDNA was obtained by 5'-RACE PCR using 5 μg of whole RNA from T-84 cells. The PCR fragment was directly sequenced and reamplified from the first strand of adult liver cDNA using an oligo-dT primer in combination with a specific primer (35 cycles); this was followed by a second amplification step (30 cycles) with nested primers. A computer-aided sequence analysis confirmed the presence of two open reading frames (ORFs) within the cDNA. The upstream ORF codes for a hypothetical precursor with a length of 113 amino acids (aa). Interestingly, the translation of the first ORF is terminated by three stop codons. A hydrophobicity plot yielded an N-terminal hydrophobic sequence of 20 aa which could be a leader peptide. The sequence of the hypothetical peptide which we called CC-2 is 46% homologous with that of MIP-1α, but contains two additional cysteine residues. The downstream ORF codes for HCC-1. Alternative splicing within intron 1 of the primary transcript yields a peptide variation of HCC-1 which contains 16 additional amino acids.

The structure of the human CC-2/HCC-1 tandem gene has been determined. The 20 kbp tandem gene which was isolated from a λ-FIX-II phage which had been isolated from a human DNA library contains seven exons, of which exons α-δ code for the hypothetical peptide CC-2, and exons 1–3 code for HCC-1. The whole region was mapped by restriction analysis. The order and orientation of the SstI restriction fragments was determined by sequencing the flanking regions of each SstI restriction site. The sequencing was performed using an automated fluorescence sequencer. Restriction fragments containing the HCC-1 gene were detected by Southern blotting with the HCC-1 cDNA as a radioactive probe. The fifteen terminal bp of the monocistronic HCC-1 cDNA (box hatched in black upstream from exon 1) do not appear in the bicistronic mRNA; therefore, they are at the same time a part of exon 1 and of intron δ. The CC-2 gene sequence was determined by primer walking. All exon/intron splicing links are in good agreement with the consensus sequences. The primer sequences were derived from the bicistronic CC-2 cDNA. The activity of the two promoters (black arrows, P1 and P2) was examined by a luciferase reporter gene assay. The transcription initiation sites were previously determined by primer extension, semi-quantitative RT-PCR and 5'-RACE.

The invention will be further illustrated by the following Examples.

In order to examine the regulation of the HCC-1 gene, the gene coding for HCC-1 was cloned using a partial HCC-1 cDNA as a hybridization probe. The sequence analysis showed that the organization of HCC-1 is in good agreement with the desribed structure made of three exons and two introns which is typical of CC chemokine genes. In order to obtain a chromosome mapping of the gene, a PCR was performed using DNA of three mouse cell hybrides each containing a defined amount of human chromosomes. The results indicated that the HCC-1 gene lies on chromosome 17 and can therefore be assigned to the subfamily of CC chemokine genes.

The examination of the activity of the HCC-1 promoter proceeded as follows. First, the transcription initiation site was determined by primer extension and semiquantitative RT-PCR analysis (PCR with reverse transcriptase), which showed that an alternative transcription initiation existed in the liver, as compared to the bone marrow and tonsils (data not shown). About 700 bp of the upstream region which presumably contained regulatory elements and a TATA box motive was cloned into the pGL-2 base vector upstream from the luciferase reporter gene. The assays for the reporter gene were performed by transfecting three different cell lines, designated as HUH-7, T 84 and RK 13, with the mentioned HCC-1 promoter/reporter gene construct as well as five 5'-truncated deletion constructs. Prior to transfection, the HUH-7 and T-84 cells were tested for expression of the HCC-1 gene, and both cell lines appeared to express the HCC-1 gene. To our surprise, only a weak promoter activity (twice to three times the background activity) could be measured in HUH-7 and T-84 cells, and a low activity (six times the background activity) was detected in RK-13 cells. However, a northern blot analysis showed strong HCC-1 mRNA signals in liver and clearly detectable signals in the large intestine (21), suggesting that the in vivo activity of the HCC-1 promoter depends on an enhancer element which was lacking in the reporter gene constructs.

In the course of a routine sequence search in a data base with expressed sequence tags (ESTs), a 5'-extended partial HCC-1 cDNA sequence was found. The additional 5'-terminal sequence was not represented in the regulatory HCC-1 upstream region which had been tested for promoter activity, which thus suggested the existence of at least one additional upstream non-translated exon. Interestingly, the fifteen 5'-terminal nucleotides of the HCC-1 cDNA (21) were not represented in the extended cDNA, proving that the fragment tested in the reporter gene assay was a part of the HCC-1 promoter. These findings surprisingly indicated that there was a second promoter region upstream from the first non-translated exon. In order to localize the second promoter within the gene, the complete extended HCC-1 cDNA was first isolated by means of the 5'-RACE PCR method using cDNA of the first strand which was synthesized from the whole RNA of T-84 cells. The product obtained contained 441 additional nucleotides as compared to the published HCC-1 cDNA sequence. It is remarkable that an EST could be found in the data base which matches the 5'-terminus of the RACE PCR product. This increases the probability that the extended cDNA corresponds to the full length. An analysis of the cDNA sequence showed that the first 5'-terminal ORF of the cDNA does not code for HCC-1, but for a new CC chemokine, CC-2. The propetide derived from this cDNA sequence consists of 113 amino acids and contains a hydrophobic N-terminal sequence of 20 amino acids with typical characteristics of a leader peptide. A sequence comparing search showed that the precursors of CC-2 and MIP-1α have 46% identical sequences. However, the hypothetical CC-2 contains six cysteine residues; recently, this was also reported for two new mouse CC chemokines, C 10 (22) and CCF 18 (23), which exhibit only low sequence homology with CC-2, but have the same cysteine pattern. The human CC chemokine I-309 (27) also contains six cysteine residues, but has not the same relative position for the two additional cysteine residues. Therefore, CC-2, C 10 and CCF 18 could form a new subgroup of CC chemokines which are conserved in humans and mice and bear an additional hypothetical disulfide linkage. In order to prove that the bicistronic transcript is also synthesized in non-transformed tissue cells, the full length cDNA was isolated from the first strand of the cDBA from adult liver and sequenced. The open reading frames for CC-2 and HCC-1 do not overlap and are 101 nucleotides apart. A sequenced cDNA clone contained 48 additional nucleotides in the downstream coding region, resulting in a peptide variation of HCC-1 containing 16 additional amino acids. This CC chemokine was called CC-3. A comparison with the genomic sequence of the HCC-1 gene showed that the additional exon lies within intron 1 and is generated by alternative splicing of the primary transcript.

Further, the structure of the genomic sequence of CC-2 was determined, and the regulation of the corresponding gene examined. Therefore, the entire insert of the λ-FIX-II phage which was originally isolated during the screening for the HCC-1 gene was mapped. A 16 kbp restriction fragment was found which contained the 5'-upstream region of the HCC-1 gene. A sequence analysis absolutely confirmed the coding region of the CC-2 nucleotide sequence within this fragment. In contrast to all known CC chemokin genes, which contain three exons separated by two introns, the coding region of the CC-2 gene consists of four exons separated by three introns. The distance between the end of exon δ of the CC-2 gene and exon 1 of the HCC-1 gene is about 12 kbp. The upstream region of exon α of the tandem gene contains a TATA box motive (TATAAAT) on position −32 with respect to the transcription initiation site, but neither GC nor CCAAT box motives. The relative activity of about 900 bp of the supposed promoter which had been cloned into the pGL-2 base vector was tested by transfecting T-84 cells. It was shown that the promoter exhibited an activity of eight to nine times the background level, which proves that the tandem gene is actively transcribed. Considering the relatively weak activity of the two promoters, one may wonder if there is a synergism between the two promoter regions, resulting in the strong constitutive expression of the HCC-1 gene in the liver and various other tissues. However, the existence of two promoter regions within the tandem gene complex suggests that the two transcriptional units of the tandem gene can also be independently activated. This stresses the importance of intergenic spacer regions which can apparently function as introns and therefore represent regions within the genome of eukaryotes for connecting closely linked genes which may become important under certain circumstances. The existence of bicistronic mature mRNAs in humans and mice was first reported for GDF-1 and a second, unknown factor, designated as UOG-1 (28). Therefore, the CC-2/HCC-1 tandem gene is the second example of a mature bicistronic human mRNA, which supports the hypothesis that polycistronic mature transcripts are probably more wide-spread in higher eukaryotes. As recently shown for the transcription factor GATA-1 (24) and some other factors (25, 26), the use of internal ATG start codons is not limited to procaryotic mRNAs, but also occurs in eucaryotic cells. It remains to prove whether the translation of eucaryotic mature polycistronic mRNAs results in multiple gene products. In view of this aspect, our work provides some new fundamental knowledge about the structure and regulation of closely linked genes and the formation of polycistronic mRNAs.

BRIEF DESCRIPTION OF THE SEQUENCES

SEQ ID NO: 1 is the nucleotide sequence of a bicistronic cDNA encoding CC-2 and CC-1.

SEQ ID NO: 2 is the nucleotide sequence of a bicistronic cDNA encoding CC-2 and CC-3.

SEQ ID NO: 3 is the sequence of the ORF encoding CC-2 present within SEQ ID NO: 1.

SEQ ID NO: 4 is the sequence of the ORF encoding CC-1 present within SEQ ID NO: 1.

SEQ ID NO: 5 is the portion of SEQ ID NO: 1 comprising the ORFs encoding CC-2 and CC-1 and the nucleotide sequence joining them. The predicted translations of the ORFs are shown.

SEQ ID NO: 6 is the amino acid sequence of CC-2 encoded by SEQ ID NOs: 1 and 3.

SEQ ID NO: 7 is the amino acid sequence of CC-1 encoded by SEQ ID NOs: 1 and 4.

SEQ ID NO: 8 is the sequence of the ORF encoding CC-2 present within SEQ ID NO: 2. The sequence is identical to SEQ ID NO: 3.

SEQ ID NO: 9 is the sequence of the ORF encoding CC-3 present within SEQ ID NO: 2.

SEQ ID NO: 10 is the portion of SEQ ID NO: 2 comprising the ORFs encoding CC-2 and CC-3 and the nucleotide sequence joining them. The predicted translations of the ORFs are shown.

SEQ ID NO: 11 is the amino acid sequence of CC-2 encoded by SEQ ID NOs: 2 and 8. The sequence is identical to SEQ ID NO: 6.

SEQ ID NO: 12 is the amino acid sequence of CC-3 encoded by SEQ ID NOs: 2 and 9.

1. Baggiolini, M. & Dahinden, C. A. Immunology Today 15,127–133 (1994)
2. Furie, M. B. & Randolph, G. J. Am. J. Pathol. 146, 1287–1301 (1995)
3. Obaru, K. et al., J. Biochem. 99, 885–894 (1986)
4. Davatelis, G. et al., J. Exp. Med. 167,1939–1944 (1988)
5. Graham, G. J. & Pragnell, I. B. Dev. Biol. 151, 377–381 (1992)
6. Verfaillie, C. M. et al., J. Exp. Med. 179, 643–649 (1994)
7. Broxmeyer, H. E. et al., J. Immunol. 147, 2586–2594 (1991)
8. Broxmeyer, H. E. et al., J. Immunol 150, 3448–3458 (1993)
9. Graham, G. J. et al., Nature 344, 442–444 (1990)
10. Uguccioni, M. et al., Eur. J. Immunol. 25, 64–68 (1995)
11. Rot, A. et al., J. Exp. Med. 176,1489–1495 (1992)
12. Cocchi, F. et al., Science 270, 1811–1815 (1995)
14. Widmer, U. et al., J. Immunol. 146, 4031–4040 (1991)
15. Widmer, U. et al., J. Immunol. 150, 4996–5012 (1993)
16. Napolitano, M. et al., J. Biol. Chem. 266,17531–17536 (1991)
17. Irving, S. G. et al., Nucleic Acids Research 18, 3261–3270 (1990)
18. Baggiolini, M. et al., Adv. Immunol. 55, 97–179 (1994)
19. Oppenheim, J. J. et al., Annu. Rev. Immunol. 9, 617–648 (1991)
20. Kelner, G. S. et al., Science 266,1395–1399 (1994)
21. Schulz-Knappe, P. et al., J. Exp. Med. 183, 295–299 (1996)
22. Orlofsky, A. et al., Cell Regul. 2, 403-xyz (1991)
23. Hara, T. et al., J. Immunol. 155, 5352–5358 (1995)
24. Calligaris, R. et al., Proc. Natl. Acad. Sci. 92,11598–11602 (1995)
25. Delmas, V. et al., Proc. Natl. Acad. Sci. 89, 4226–4230 (1992)
26. Scholer, H. R. et al., Nature 344, 435–439 (1990)
27. Miller, M. D. et al., J. Immunol. 143, 2907–2916 (1989)
28. Lee, S. J., Proc. Natl. Acad. Sci. 88, 4250–4254 (1991)

What is claimed is:

1. An isolated nucleic acid molecule comprising a nucleotide sequence encoding the amino acid sequence of chemokine CC-2 as shown in SEQ ID NO: 6.

2. A nucleic acid molecule according to claim 1, comprising the nucleotide sequence shown in SEQ ID NO: 3.

3. An isolated nucleic acid molecule comprising a nucleotide sequence encoding the amino acid sequence of chemokine CC-3 as shown in SEQ ID NO: 12.

4. A nucleic acid molecule according to claim 3, comprising the nucleotide sequence as shown in SEQ ID NO: 9.

5. An isolated bicistronic nucleic acid molecule comprising nucleotide sequences encoding the amino acid sequence of chemokine CC-2 as shown in SEQ ID NO: 6 and the amino acid sequence of chemokine CC-3 as shown in SEQ ID NO: 12.

6. A nucleic acid molecule according to claim 5, comprising the nucleotide sequence shown in SEQ ID NO: 10.

7. A nucleic acid molecule according to claim 6, comprising the nucleotide sequence shown in SEQ ID NO: 2.

8. An isolated bicistronic nucleic acid molecule comprising nucleotide sequences encoding the amino acid sequence of chemokine CC-2 as shown in SEQ ID NO: 6 and the amino acid sequence of chemokine CC-1 as shown in SEQ ID NO: 7.

9. A nucleic acid molecule according to claim 8, comprising the nucleotide sequence shown in SEQ ID NO: 5.

10. A nucleic acid molecule according to claim 9, comprising the nucleotide sequence shown in SEQ ID NO: 1.

11. An isolated chemokine CC-2 polypeptide comprising the amino acid sequence shown in SEQ ID NO: 6 or an amidated, acetylated, phosphorylated, or glycosylated derivative thereof.

12. An isolated chemokine CC-3 polypeptide comprising the amino acid sequence shown in SEQ ID NO: 12 or an amidated, acetylated, phosphorylated, or glycosylated derivative thereof.

13. A pharmaceutical composition comprising a chemokine polypeptide according to claim 11 and a pharmaceutically acceptable carrier.

14. A pharmaceutical composition comprising a chemokine polypeptide according to claim 12 and a pharmaceutically acceptable carrier.

15. A pharmaceutical composition comprising chemokine CC-2 and CC-3 polypeptides, wherein the CC-2 polypeptide comprises the amino acid sequence shown in SEQ ID NO: 6 or is an amidated, acetylated, phosphorylated, or glycosylated derivative thereof; and the CC-3 polypeptide comprises the amino acid sequence shown in SEQ ID NO: 12 or is an amidated, acetylated, phosphorylated, or glycosylated derivative thereof.

* * * * *

UNITED STATES PATENT AND TRADEMARK OFFICE
CERTIFICATE OF CORRECTION

PATENT NO.    : 6,180,773 B1
DATED         : January 30, 2001
INVENTOR(S)   : Wolf-Georg Forssmann et al.

It is certified that error appears in the above-identified patent and that said Letters Patent is hereby corrected as shown below:

Column 4,
Line 39, change "cDBA" TO -- cDNA --.

Signed and Sealed this

Thirtieth Day of October, 2001

Attest:

NICHOLAS P. GODICI
Attesting Officer       Acting Director of the United States Patent and Trademark Office